United States Patent [19]

Kibby et al.

[11] Patent Number: 4,492,774

[45] Date of Patent: Jan. 8, 1985

[54] METHOD FOR CONVERTING SYNTHESIS GAS USING AN ACTIVATED COBALT-SUBSTITUTED LAYERED ALUMINOSILICATE

[75] Inventors: Charles L. Kibby, Gibsonia; Thaddeus P. Kobylinski, Prospect, both of Pa.

[73] Assignee: Gulf Research & Development Company, Pittsburgh, Pa.

[21] Appl. No.: 453,139

[22] Filed: Dec. 27, 1982

[51] Int. Cl.³ .............................................. C07C 1/04
[52] U.S. Cl. .................................... 518/713; 518/715
[58] Field of Search ............................... 518/713, 715

[56] References Cited

U.S. PATENT DOCUMENTS 3,252,889  5/1966  Capell et al. ..................... 208/120
3,966,642  6/1976  Black et al. ....................... 252/455
4,304,871 12/1981  Brennan et al. .................. 518/715
4,410,637 10/1983  Kortbeek et al. ................. 518/715

OTHER PUBLICATIONS

Lapidus et al., Chem. Abst. 94: 211105s, (1981).

Primary Examiner—Howard T. Mars
Attorney, Agent, or Firm—Deane E. Keith; Forrest D. Stine

[57] ABSTRACT

A process for converting synthesis gas to liquid hydrocarbons using a catalyst prepared from synthetic layered aluminosilicate having a montmorillonite-type structure and containing cobalt substituted in the crystal lattice and activated for the conversion by a sequential reduction, oxidation and reduction treatment.

10 Claims, No Drawings

METHOD FOR CONVERTING SYNTHESIS GAS USING AN ACTIVATED COBALT-SUBSTITUTED LAYERED ALUMINOSILICATE

SUMMARY OF THE INVENTION

Synthesis gas is converted to a liquid product predominating in branched hydrocarbons and internal olefins using an activated, cobalt-substituted, layered aluminosilicate catalyst. The synthetic aluminosilicate is prepared with cobalt substituent in the crystal lattice by a hydrothermal process. The semicrystalline product, a synthetic montmorillonite-type material, is ordered in two directions in a layered structure. This material is activated as a Fischer-Tropsch catalyst for the synthesis gas conversion by a multi-stage, alternate reduction-oxidation procedure.

DESCRIPTION OF THE INVENTION

Synthesis gas comprising a mixture of hydrogen and carbon monoxide in appropriate proportions can be converted to liquid hydrocarbons in the presence of a suitable catalyst by the Fischer-Tropsch synthesis. Commercial plants have operated in Germany, South Africa and in other countries for the production of liquid fuels from coal-derived synthesis gas using particular catalysts. For example, the German commercial operation utilized a precipitated cobalt-thoria/magnesia-kieselguhr catalyst in a fixed bed. The product of this and other commercial ventures has been a liquid hydrocarbon product predominating in a gasoline range fraction comprised almost exclusively of normal hydrocarbons, primarily paraffins and terminal olefins. Since branched hydrocarbons have a higher octane rating than straight-chain hydrocarbons, they are the desired molecular structure for fuel use in gasoline-powered internal combustion engines. As a result, substantial additional processing, including isomerization, of these Fischer-Tropsch gasolines has been necessary. We have discovered a novel Fischer-Tropsch catalyst which synthesizes a gasoline range fraction predominating in high octane, branched hydrocarbons and internal olefins.

U.S. Pat. No. 3,252,757 describes the hydrothermal preparation of a synthetic aluminosilicate having a mixed layered structure. The randomly alternating layers are of montmorillonite-like and mica-like clay mineral having crystal lattices comprising silica tetrahedra and alumina octahedra. The dehydration of this synthetic mineral and the use of the dehydrated product as a cracking catalyst in the cracking of hydrocarbons is described in U.S. Pat. No. 3,252,889. The catalyst is described in this patent as a crystalline aluminosilicate which is ordered in two directions, that is, is of lamellar or of a layered or stacked sheet structure.

In U.S. Pat. No. 3,966,642 a synthetic aluminosilicate is made hydrothermally by the general method described in U.S. Pat. No. 3,252,757 except that a nickel or cobalt salt is added to the initial reaction mixture in order to incorporate nickel or cobalt internally into the crystal lattice. After forming the synthetic aluminosilicate by an appropriate heat activation treatment, a hydrogenation component with nickel and cobalt being preferred hydrogenating metals, is deposited on the aluminosilicate by impregnation followed by calcination. However, the hydrogenation component, being external, does not form a part of the crystal structure of the resulting mineral in contrast with the nickel or cobalt used in the initial reaction mixture. This metals-modified product is shown by the patent to be useful as a hydrocarbon conversion catalyst for the hydrocracking and hydroisomerization of hydrocarbons.

We have discovered a synthesis gas conversion process using a novel synthetic cobalt aluminosilicate catalyst. A hydrothermally prepared semicrystalline montmorillonite-type material having cobalt incorporated into the crystal lattice is activated for the conversion. Surprisingly, the predominant fraction in the liquid hydrocarbon product comprises a gasoline range mixture of branched hydrocarbons and internal olefins. The catalyst activation procedure includes a multi-stage reduction-oxidation treatment of the catalyst. We have found that the activation requires a minimum of three stages, that is, a reduction of the catalyst, the oxidation of the catalyst, and finally, another reduction of the catalyst. Additional series of oxidation and reduction treatments can be applied to the catalyst, as desired, ending in a final reduction treatment.

The hydrothermally produced cobalt aluminosilicate has the following general formula prior to its activation treatment:

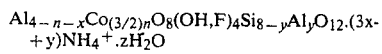

$$Al_{4-n-x}Co_{(3/2)n}O_8(OH,F)_4Si_{8-y}Al_yO_{12} \cdot (3x+y)NH_4^+ \cdot zH_2O$$

where n is between about 0.02 and about 4, preferably between about 2 and about 3; x is up to about 1, preferably between about 0.1 and about 0.2; n+x is between about 0.02 and about 4, preferably between about 2 and about 3; y is between about 0.05 and about 2, preferably between about 0.5 and about 2; and z is up to about 10. In the above formula, the predominant amount of aluminum and the cobalt, the hydroxyl and the fluorine are in the octahedral layers, while the silicon and a minor amount of aluminum are in the tetrahedral layers. The ammonium and water are primarily positioned between the layers.

When the composition of the above formula is heated to an elevated temperature in the activation treatment or in an optional, pre-activation calcination stage, a minor change in the above formula will result. This heating will drive off most or all of the water of hydration. Also, it will drive off most of the ammonia as ammonium hydroxide, the amount depending, in part, on the severity of the heating, and the hydroxyl content will correspondingly decrease. The activation treatment will effect subtle physical and chemical changes in the catalyst, including a reduction in the oxygen content as expressed in the above formula.

The reduction treatments are carried out at an elevated temperature in a reducing atmosphere, preferably hydrogen, and the oxidation treatment is carried out at an elevated temperature in an oxidizing atmosphere, preferably air or diluted air. The use of diluted air may be desirable as a means of controlling the highly exothermic oxidation reaction. The initial reduction is carried out at a temperature between about 500° and about 750° C., preferably between about 550° and about 650° C. for sufficient time to effect a significant reduction of the cobalt aluminosilicate as evidenced by oxygen loss. The reduced material is oxidized at a temperature between about 100° and about 600° C., preferably between about 200° and about 500° C., for sufficient time to cause a significant increase in the oxygen content of the material. Subsequent oxidation stages, if any, are carried out at the same conditions. The second and any subsequent reduction stages are carried out at a temperature between about 200° and about 500° C., preferably between about 300° and about 400° C., for sufficient time to effect a significant reduction in the oxygen content of the catalyst. The physical and chemical characteristics of the activated catalyst will be a function both of its composition and the temperature-time relationships in the various stages of the activation treatment.

The hydrated precursor composition of the above formula can be prepared, in general, by the hydrothermal process as described in U.S. Pat. No. 3,252,757 and by the modified hydrothermal process of U.S. Pat. No. 3,966,642, which describes the incorporation of cobalt into the crystal lattice. Both of these patents are incorporated herein by reference.

The activity of the catalyst can be further enhanced by impregnating silver, gold or a Group VIII metal selected from platinum, palladium, ruthenium, and iridium, preferably ruthenium, onto the surface of the catalyst. Preferably this impregnation is done following the oxidation procedure and prior to the final reduction procedure. Any amount of the noble metal up to about 5 weight percent of the total catalyst can be used but preferably, when used, the noble metal will constitute between about 0.05 and about 0.5 weight percent of the catalyst. When a noble metal is used, the mol ratio of cobalt to noble metal is suitably from about 10:1 to about 1,000:1, preferably from about 50:1 to about 200:1.

The synthesis gas reaction using the catalysts of this invention can occur in a fixed-, fluid- or moving-bed type of operation; however, a fixed-bed operation is preferred. In the fixed-bed operation, the charge gases would normally be passed downflow through the bed of catalyst with the reaction product being collected by suitable condensation techniques, after which the products are separated by fractionation.

The catalyst of the present invention has an average particle diameter which depends upon the type of reactor used of from about 0.01 to about 6 millimeters; preferably from about 1 to about 6 millimeters for a fixed bed; preferably about 0.02 to about 0.15 being preferred for a fluidized bed, and from about 0.01 to about 0.05 millimeters for a slurry.

The charge stock used in the process of this invention is a mixture of carbon monoxide and hydrogen. The source of the carbon monoxide and hydrogen to be used in the charge stocks for this invention is not critical and can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, but it may be present as a diluent gas. Sulfur compounds in any form are deleterious to the life of the catalyst and should be removed.

The molar ratio of hydrogen to carbon monoxide in the charge stock can be, for example, from about 0.5:1 to about 4:1 or higher, e.g., 10:1, preferably from about 1:1 to about 2.5:1, with 1.5:1 to about 2:1 being especially preferred.

The reaction temperature is suitably from about 160° to about 350° C., preferably from about 175° to about 250° C., and most preferably from about 185° to about 215° C. The total pressure is from about 1 to about 100 atmospheres, preferably from about 1 to about 50 atmospheres, and most preferably from about 1 to about 20 atmospheres. The hydrogen partial pressure is from about 0.1 to about 30 atmospheres, preferably from about 0.5 to about 25 atmospheres, and most preferably from about 1 to about 20 atmospheres.

The gas hourly space velocity based upon the total amount of feed is less than 20,000 volumes of gas per volume of catalyst per hour, preferably from about 100 to about 5,000 v/v/hour, with from about 200 to about 2,500 v/v/hour being especially preferred. If desired, pure synthesis gas can be employed or, alternatively, an inert diluent, such as nitrogen, carbon dioxide, methane, steam or the like can be added. As used herein, the expression "inert diluent" indicates that the diluent is non-reactive under the reaction conditions herein disclosed or is a normal reaction product.

The invention will be further described with reference to the following experimental work.

EXAMPLE 1

The catalyst preparation is described.

A saturated aqueous solution of 161 g of $AlCl_3 \cdot 6H_2O$ in two liters of water was slurried with 1,840 g of a silicic acid solution, forming a silica, $SiO_2$, to alumina, $Al_2O_3$, weight ratio of 4.7. A silica-alumina gel was precipitated by the addition of the slurry to one liter of an ammonium hydroxide solution having a pH of 8.0, which was maintained by the addition of ammonium hydroxide as needed. The gel was filtered and washed with distilled water to remove chloride impurity. A 50 g portion of the washed gel was then slurried in 225 ml of water containing 60 g of cobalt acetate, 0.78 g of ammonium fluoride, and 0.42 g of hydrogen fluoride, with stirring and at a pH of 8.0, which was maintained by the addition of ammonium hydroxide as needed. The gel was placed in an autoclave and quickly heated to 300° C. at a pressure of 1,240 psig (8.55 MPa). After four hours in the autoclave the gel was cooled, filtered and dried at 120° C. After calcining in air at 500° C. for 4 hours, it was a hard, wine-red solid having a nominal cobalt to $SiO_2$—$Al_2O_3$ ratio of 0.30.

The catalyst was reduced in a hydrogen atmosphere at 400° C. for two hours, producing a weight loss of 1.57 percent, and reoxidized at 500° C. in air for two hours to result in a 1.63 percent weight gain. It was next reduced in hydrogen at 500° C. for 16 hours, causing a weight loss of 3.14 percent with a reoxidation in air resulting in a weight gain of 2.61 percent. The catalyst was then reduced in hydrogen at 600° C. for 16 hours, effecting a weight loss of 8.5 percent with reoxidation in air at 500° C. for two hours, causing a weight gain of 8.1 percent. A final reduction in hydrogen at 400° C. for 16 hours resulted in a weight loss of four percent.

The calcination step described in the above catalyst preparation was carried out prior to the first reduction step. Calcination effects a dehydration of the catalyst and drives off a substantial portion of the ammonia as ammonium hydroxide. However, it is not necessary to have a separate calcination step. Rather the calcination and the first reduction stage can be effectively accomplished concurrently.

EXAMPLE 2

The catalyst prepared in Example 1 was used for the conversion of synthesis gas. The conversion was carried out in a glass microreactor at atmospheric pressure using a 0.5 g bed of the catalyst. A hydrogen and carbon monoxide mixture in a 1:1 mol ratio was fed to the reactor at a flow rate of 480 cubic centimeters of the gas per gram of catalyst per hour. After the reaction stabilized, conversions were carried out at three different temperatures, and the products were analyzed by gas chromatography. The product distribution and relative reaction rates are set out in Table I.

TABLE I

|  | Temperatures, °C. | | |
|---|---|---|---|
|  | 175 | 185 | 195 |
| Yield, wt % | | | |
| $C_1$-$C_4$ | 22 | 25 | 34 |
| $C_5$-$C_{11}$ | 54 | 60 | 57 |
| $C_{12}+$ | 24 | 15 | 9 |
| Relative rate, mg/g/hr | | | |
| $C_1$-$C_4$ | 0.3 | 0.5 | 1.1 |
| $C_5$-$C_{11}$ | 0.7 | 1.2 | 1.8 |
| $C_{12}+$ | 0.3 | 0.3 | 0.3 |

The major product in the five carbon and higher product was found to be isoalkanes and isoolefins. There was also a relatively high proportion of internal olefins in the product mixture.

It is to be understood that the above disclosure is by way of specific example and that numerous modifications and variations are available to those of ordinary skill in the art without departing from the true spirit and scope of the invention.

What is claimed as the invention:

1. A method for converting synthesis gas to a product predominating in liquid hydrocarbons which comprises contacting said synthesis gas under conversion conditions with a synthesis gas conversion catalyst obtainable by the multi-stage activation of a layered aluminosilicate having cobalt incorporated into the crystal lattice and having the general formula:

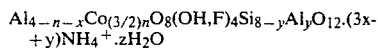

where n is between about 0.02 and about 4; x is up to about 1; n+x is between about 0.02 and about 4; y is between about 0.05 and about 2; and z is up to about 10; said activation procedure comprising the steps:

(a) heating the layered aluminosilicate in a reducing atmosphere at a temperature between about 500° and about 750° C. until a significant amount of the cobalt is reduced;

(b) heating the reduced aluminosilicate in an oxidizing atmosphere at a temperature between about 100° and about 600° C. until a significant amount of the cobalt is oxidized, and (c) heating the oxidized aluminosilicate in a reducing atmosphere at a temperature between about 200° and about 500° C. until a signficant quantity of the cobalt is reduced.

2. The synthesis gas conversion process in accordance with claim 1 in which said layered aluminosilicate is calcined in air at an elevated temperature between about 200° and about 500° C.

3. The synthesis gas conversion process in accordance with claim 1 where n is between about 2 and about 3; x is between about 0.1 and about 0.2; n+x is between about 2 and about 3; and y is between about 0.5 and about 2.

4. The synthesis gas conversion process in accordance with claim 1 in which the reducing temperature in step (a) is between about 550° and about 650° C., the oxidizing temperature of step (b) is between about 200° and about 500° C., and the reducing temperature of step (c) is between about 300° and about 400° C.

5. The synthesis gas conversion process in accordance with claim 1 in which at least one additional oxidation treatment and at least one additional reduction treatment are carried out on the catalyst at the conditions specified in steps (b) and (c), respectively.

6. The synthesis gas conversion process in accordance with claim 1 wherein the molar ratio of hydrogen to carbon monoxide is from about 0.5:1 to about 4:1.

7. The synthesis gas conversion process in accordance with claim 3 wherein the molar ratio of hydrogen to carbon monoxide is from about 1:1 to about 2.5:1.

8. The synthesis gas conversion process in accordance with claim 1 wherein the synthesis gas conversion conditions include a temperature of from about 160° to about 350° C.

9. The synthesis gas conversion process in accordance with claim 7 wherein the synthesis gas conversion conditions include a temperature of from about 170° to about 250° C.

10. The synthesis gas conversion process in accordance with claim 1 wherein the total pressure is from about 1 to about 50 atmospheres.

* * * * *